United States Patent [19]

Napoli et al.

[11] Patent Number: 5,409,014
[45] Date of Patent: Apr. 25, 1995

[54] FLUID METER

[75] Inventors: Michael P. Napoli, Bellevue, Wash.; Charles C. Holtan, Newberg; Richard G. Kluempke, Tigard, both of Oreg.

[73] Assignee: Dravon Medical, Inc., Clackamas, Oreg.

[21] Appl. No.: 106,405

[22] Filed: Aug. 13, 1993

[51] Int. Cl.⁶ .............................................. A61B 5/00
[52] U.S. Cl. .................................................. 128/762
[58] Field of Search ....................... 128/760, 762, 767; 604/257, 260, 262, 317, 322–326

[56] References Cited

U.S. PATENT DOCUMENTS

| Re. 26,964 | 4/1964 | Coanda . | |
| D. 303,714 | 9/1989 | Manschot . | |
| 3,661,143 | 5/1972 | Henkin . | |
| 3,699,964 | 10/1972 | Ericson . | |
| 3,800,795 | 4/1974 | Walker . | |
| 3,831,453 | 8/1974 | McWhorter | 73/427 |
| 4,305,290 | 12/1981 | Taylor | 128/762 |
| 4,305,405 | 12/1981 | Meisch | 128/762 |
| 4,564,361 | 1/1986 | Akiyama | 604/265 |
| 4,743,236 | 5/1988 | Manschot | 128/762 |
| 5,119,675 | 6/1992 | Mohiuddin | 128/771 |

FOREIGN PATENT DOCUMENTS

PCT/US91/-09314 6/1991 WIPO .

Primary Examiner—Max Hindenburg
Attorney, Agent, or Firm—Klarquist Sparkman Campbell Leigh & Whinston

[57] ABSTRACT

A fluid meter for measuring fluids such as urine includes a connector for connecting and disconnecting a urine collection bag thereto. The fluid meter may also include a connector for connecting and disconnecting the meter from a catheter drain tube. In the preferred embodiment, the urine meter includes a container having an inlet and outlet. A male connector is operatively attached to the container outlet for connecting and disconnecting the container from a female connector attached to the urine collection bag. Similarly, a female connector is operatively attached to the container inlet for connecting and disconnecting the container from a male connector attached to the drain tube. As an additional feature, the female connector of the urine collection bag may be connected directly to the male connector of the drain tube with the urine meter disconnected therefrom.

14 Claims, 5 Drawing Sheets

FLUID METER

FIELD OF INVENTION

The present invention relates to a fluid meter and particularly to a urine meter for measuring volumes of urine.

BACKGROUND OF THE INVENTION

Physicians and hospital personnel routinely collect urine from patients for measuring the urine output of patients and for urine sampling. Urinary measuring devices, such as urine meters, are often used for post-operative patients and for patients having urological disorders. Urine meters are also referred to in the industry as urinometers and urometers.

When using a urine meter to collect urine from a patient, the patient is first catheterized in the urinary tract and a proximal catheter end of a catheter is connected to an inlet of the urine meter through a flexible catheter drainage tube. The urine drains by gravity from the patient through the drainage tube into the urine meter so that the urine output may be measured in the urine meter. The urine meter has a transparent front surface and measuring scales attached to one side so that medical personnel may estimate the volume of urine collected by reading the measuring scales. When the urine meter is filled with urine or when the urine meter needs to be emptied, urine may flow into a urine collection bag permanently attached to the urine meter. The bag typically has a drain valve that allows it to be emptied when it becomes full. Additionally, most urine meters are permanently attached to the catheter drain tube.

There are several drawbacks to urine meters currently available on the market. Due to their high cost, urine meters are utilized for a long period of time. This means that the collection bag is repeatedly filled and emptied, increasing a risk of infection. Additionally, it is necessary to disturb the patient each time the urine meter is replaced.

Therefore, an object of the present invention is to provide a urine meter that may be easily removed or installed without unduly disturbing the patient. Another object of this invention is to provide a urine meter and collection bag which may be connected to and disconnected from each other to permit easy replacement of the collection bag. Still another object of the invention is to provide a collection bag, urine meter and catheter drain tube which are constructed to permit the urine meter to be removed and the drain tube to be connected directly to the collection bag, if desired.

SUMMARY OF THE INVENTION

The present invention is a fluid meter for insertion between a fluid source such as a catheter drain tube and a fluid collector such as a fluid collection bag, such as for measuring and collecting inlet and an outlet. The container may have a first metering chamber adjacent to the inlet for receiving fluid therefrom and a second metering chamber adjacent to the outlet. The first metering chamber is in fluid communication with the metering chamber. A first connector is operatively attached to the container outlet for connecting and disconnecting the container from the fluid collection bag. A second connector may be operatively attached to the container inlet for connecting the container to and disconnecting the container from the catheter drain tube.

In one embodiment of the invention, the connectors may be constructed to allow the catheter drain tube to be connected to the collection bag with the fluid meter removed. For example, the first connector may be one part of a two part connector, with the other connector part being attached to the collection bag. Similarly, the second connector may be one part of a two part connector, the other connector part being attached to the drain tube. The first and second connectors are constructed such that the connector part attached to the drain tube is adapted to connect to the connector part attached to the collection bag with the fluid meter disconnected from the drain tube and collection bag.

The invention in various embodiments thus provides great versatility in measuring and collecting bodily fluids from a patient. If it is desirable to measure fluid flow, the catheter drain tube may be connected to a fluid meter and the fluid meter to the collection bag. If it is desirable to change the collection bag, the fluid meter may be simply disconnected from the present bag and reconnected to another bag. If the need for a fluid meter has ended, it may be removed by simply disconnecting the drain tube and the collection bag from the meter and connecting the tube and bag together.

The foregoing and other objects, features, and advantages of the invention will become more apparent from the following detailed description of a preferred embodiment which proceeds with reference to the accompanying drawings.

DETAILED DESCRIPTION

Figure 1:
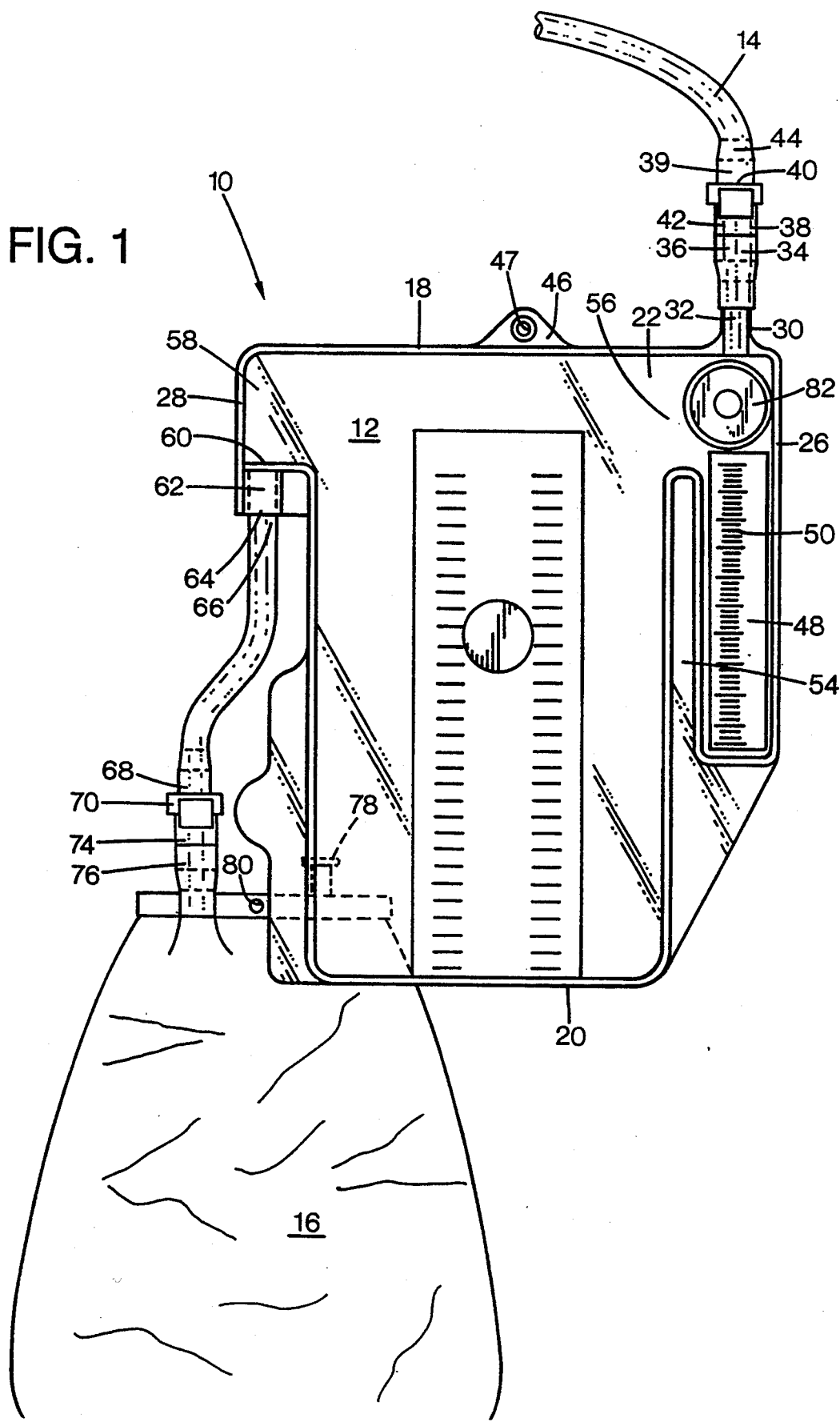
FIG. 1 is a front view of a fluid meter according to the invention, shown inserted between a catheter drain tube and a fluid collection bag.

FIG. 1 shows a fluid meter 10 constructed in accordance with the present invention, inserted between a fluid source such as a catheter drain tube 14 and a fluid collector such as a fluid collection bag 16. The meter 10 includes a container 12 that is in fluid communication with drain tube 14 and collection bag 16 so that fluid may flow from drain tube 14 through container 12 into collection bag 16. The invention's present use is for urine meters and is further described in that context. However, it should be understood that the legal scope of the invention is limited only by the claims and not by this description of a preferred embodiment.

Figure 5:
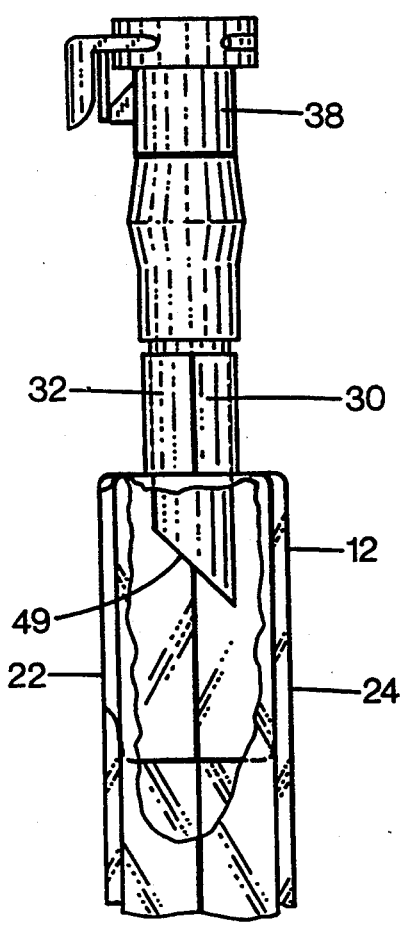
FIG. 5 is a partial side view of the fluid meter of FIG. 1.

Container 12 may be made of a durable and lightweight material such as a molded transparent thermoset or thermoplastic material. It is to be understood that other materials may be used such as non-transparent polymer, metal and paper based materials. The container may be made by a vacuum, compression or injection molding process or any other equivalent molding process known to those skilled in the art. The container has a top wall 18 and an opposite bottom wall 20. With additional reference to FIG. 5, the top and bottom wall 18, 20 are connected by a transparent front wall 22, rear wall 24 and opposite side walls 26, 28.

The top wall 18 has an annular inlet protrusion 30 defining an inlet 32. The inlet protrusion 30 extends away from container 12 and a short flexible inlet tube 34 is preferably, but not necessarily, inserted into the protrusion and secured thereto by, for example, an adhesive. The inlet tube 34 extends into the first meter chamber 48 and has a slanted free end 49 (FIG. 5) for directing fluid flowing therethrough into the first metering chamber 48. The slanted free end 49 also reduces the surface tension of the fluid to create a drip into the first metering chamber 48. It is apparent that the slanted free end 49 may be part of the container 12 or supplied as a separate component. The other end of inlet tube 34 is operatively connected to a connector such as female connector part 38. An example of such a female connector is shown and described in U.S. Pat. No. 5,052,725, which is hereby incorporated by reference, although it should be understood that other types of equivalent connectors are acceptable. The female connector part may be sealingly attached to an inside of inlet tube 34 to prevent leakage of urine flowing in inlet tube 34 and any accidental disconnection of female connector part 38 from inlet tube 34.

The female connector part 38 is one connector part of a two part connector assembly. The other connector part is a suitable male connector part 39 that is operatively attached to catheter drain tube 14. In general, female connector part 38 has a male-connector-receiving opening 40 formed therein for receiving a tubular extension 42 of male connector part 39 sealingly attached to a downstream end 44 of catheter drain tube 14. The positions of the male connector part 39 and female connector part 38 may, of course, be reversed, with the part 39 attached to inlet tube 34 and the part 38 attached to drain tube 14. The other end of catheter drain tube 14 may be connected to a catheter (not shown) which in turn may be inserted into a patient's body for collecting and conveying fluid such as urine therefrom. A clamp (not shown) is preferably attached to catheter drain tube 14 to stop any flow of fluid therethrough before the urine meter is disconnected from the drain tube. The clamp also prevents bacteria from migrating back through the drain tube 14. The clamp may be removed to allow fluid to flow through drain tube 14. In an alternative embodiment, male connector part 39 may have a shut off valve incorporated therein to prevent bacteria from migrating back up the drain tube 14.

Figure 2:
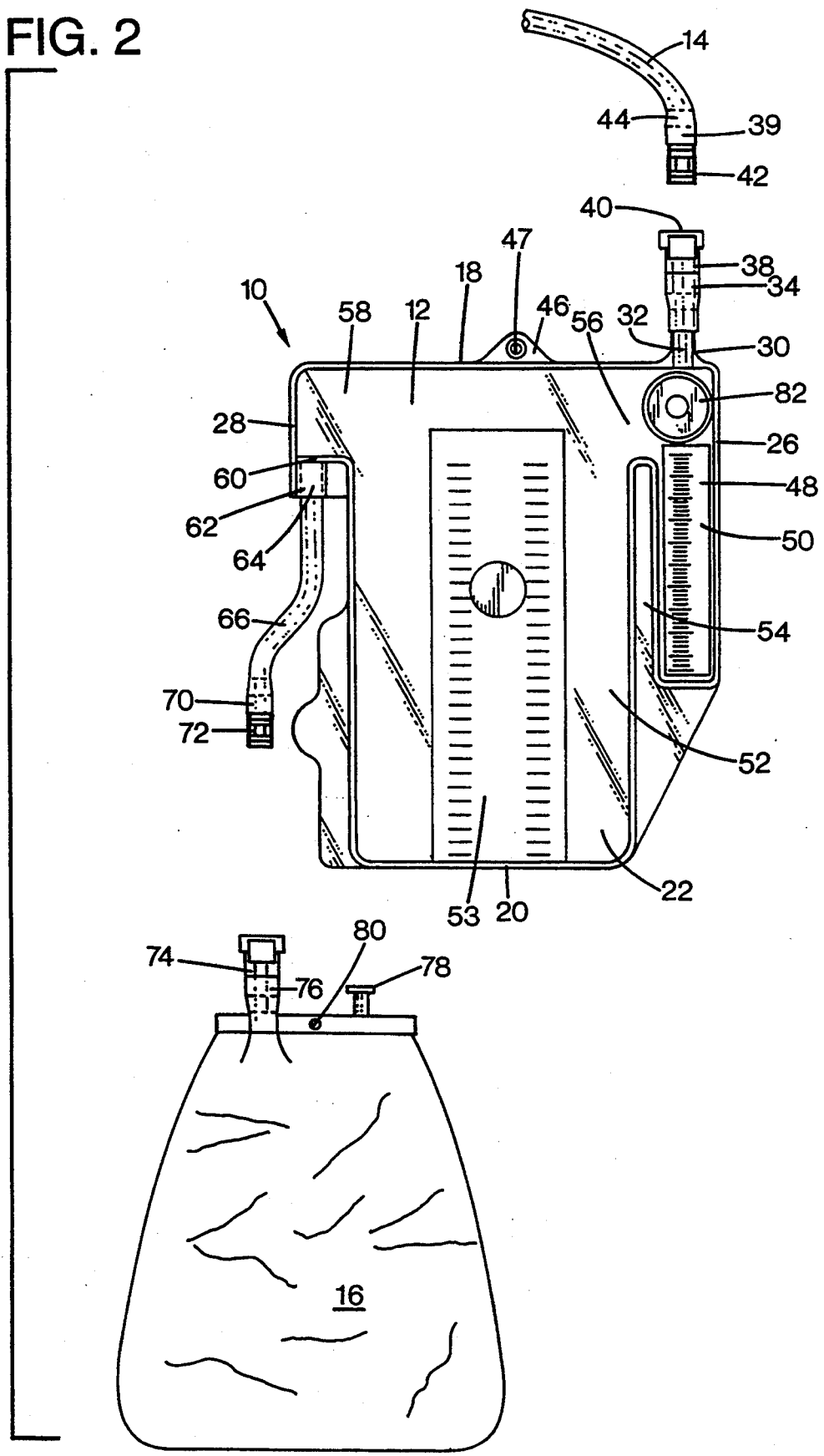
FIG. 2 shows the fluid meter of FIG. 1 disconnected from the catheter drain tube and fluid collection bag.

Referring to FIG. 2, a notable feature of the present invention is that male connector part 39 may be adapted to be connected to and disconnected from female connector part 38. The connection and disconnection of male connector part 39 is convenient and easy to perform which makes it unnecessary to disturb the patient when it is time, for example, to replace urine meter 10. Female connector part 38 and male connector part 39 may be held together in a variety of ways such as by a snap-on mechanism disclosed in U.S. Pat. No. 5,052,725. The connector parts 38, 39 each has a passageway formed therein to allow urine to be conveyed therethrough and are adapted to sealingly engage each other to prevent any leakage of fluid flowing from catheter drain tube 14 into container 12. As is apparent, urine meter 10 may be permanently attached to drain tube 14.

The top wall 18 of container 12 has a hanger tab 46 defining an opening 47 so that container 12 may be supported by a conventional hanger (not shown) or equivalent supporting means inserted through hole 47. Urine meters are often mounted on a stand, cart or perhaps a patient's bed frame by such a hanger so that the weight of the meter does not pull it away from the drain tube 14. The hanger is preferably designed to maintain the container 12 in an upright position to prevent contact between the fluid in the container and the free end 49.

As shown in the figures, the container 12 has the first metering chamber 48 adjacent inlet 32 for receiving and measuring small amounts of urine flowing through inlet 32. The transparent front wall 22 has a measuring scale 50 adhered thereto for measuring volumes of urine received by first metering chamber 48 such as volumes up to 50 milliliters (ml). As is apparent, first metering chamber 48 may be smaller or larger than 50 ml.

The container 12 also has a second, metering chamber 52 in fluid communication with first metering chamber 48. Metering chamber 52 is, preferably, but not necessarily, larger than first metering chamber 48. The metering chamber may have a measuring scale 53 for measuring urine volumes of up about 640 ml or more. As is apparent, metering chamber 52 may be used to measure volumes less than 640 ml. The metering chamber 52 is partially separated from first metering chamber 48 by an upright separation wall 54 so that a passageway 56 is formed near the tops of chambers 48 and 52 between separation wall 54 and top wall 18 of container 12. Thus, when first metering chamber 48 is filled with urine, any additional urine overflows through passageway 56 into metering chamber 52.

The sidewall 28 of container 12 defines a hollow extension 58 adjacent top wall 18. The extension has a bottom surface 60 including an outlet protrusion 62 defining an outlet 64. In the illustrated embodiment, outlet protrusion 62 is substantially parallel to inlet protrusion 30 but extending in a direction opposite inlet protrusion 30. As is apparent, outlet protrusion 62 may extend in other directions such as in the same direction or in a direction perpendicular to the direction of inlet protrusion 30. The container 12 may be tilted (FIG. 3) to discharge urine 63 from urine meter 10 through outlet 64 into urinary collection bag 16 as explained below.

A flexible discharge tube 66 has an upstream end 68 operatively attached to outlet protrusion 62 and a downstream end 70 operatively attached to a connector such as male connector part 72. The male connector part 72 may be substantially similar to male connector part 39 attached to catheter drain tube 14.

Referring again to FIG. 2, male connector part 72 is adapted to be connected to and disconnected from a female connector part 74 operatively connected to an inlet portion 76 of urine collection bag 16. Again, the positions of the male connector part 72 and the female connector part 74 may be reversed. The urine collection bag may be of a type typically used in the medical profession for collecting urine. The collection bag may have a drain mechanism (not shown) for draining fluid therefrom. Urine collection bag 16 preferably has a vent 78 for allowing air, but not liquids such as urine, to flow in and out of the bag to compensate for pressure changes as the bag is filled with urine. The bag structure also defines a hanger opening 80 so that the bag may also be supported on a hanger in a manner similar to which the urine meter 10 is supported.

Figure 4:
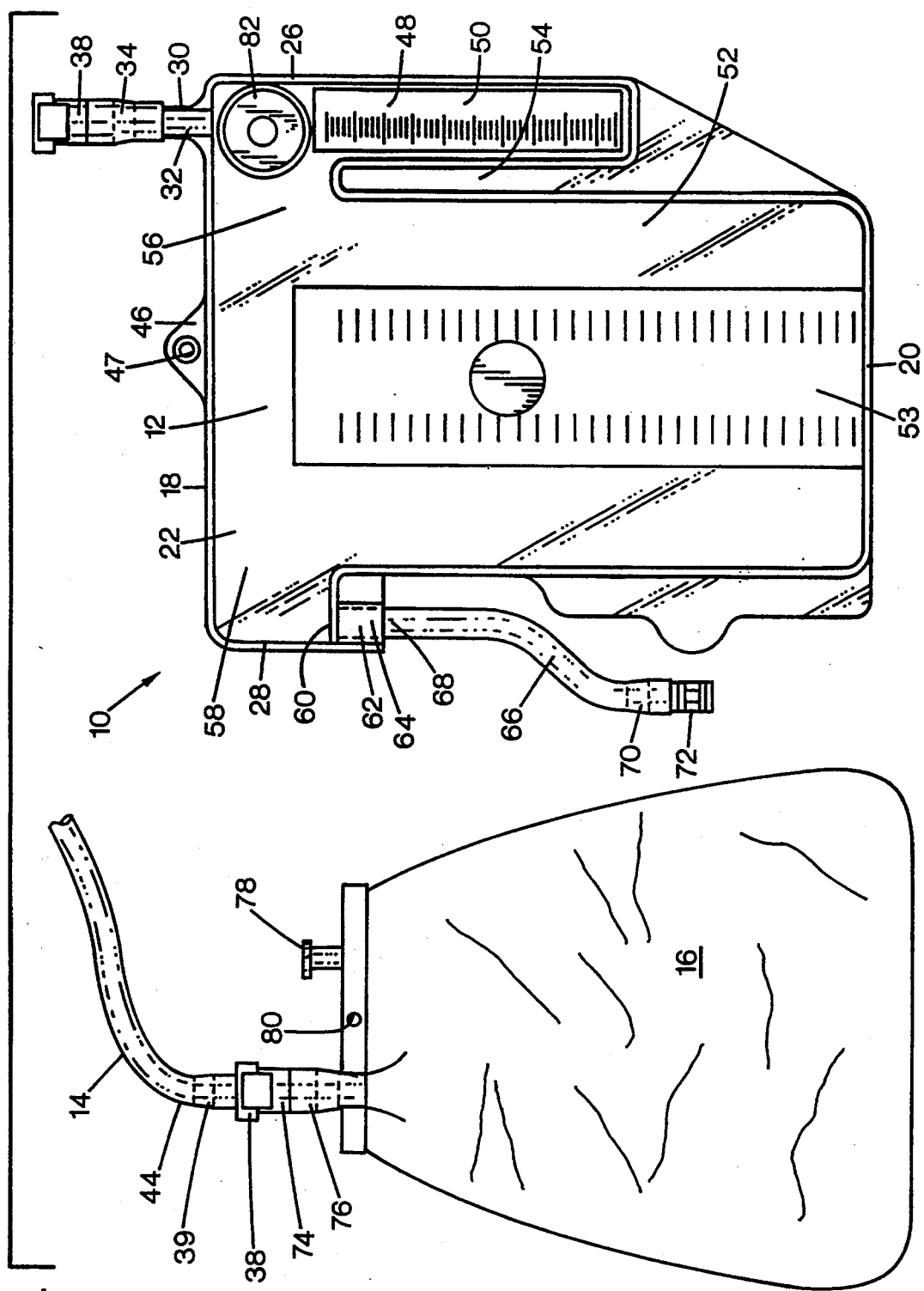
FIG. 4 depicts the fluid collection bag connected to the catheter drain tube with the fluid meter removed.

Referring to FIG. 4, another notable feature of the present invention is that female connector 74 also connects to male connector part 39 of catheter drain tube 14 with urine meter 10 disconnected from catheter drain tube 14. Female connector part 74 may be connected directly to male connector part 39 of catheter drain tube 14 (FIG. 4) or indirectly through means other than the meter 10. Either way, urine may flow from drain tube 14 into urine collection bag 16 without the need for urine meter 10. Since the male connector parts are easy to connect to and disconnect from the female connector parts, urine meter 10 may conveniently be disconnected from and reconnected to catheter drain tube 14 and urine collection bag 16 without having to withdraw the catheter or otherwise disturbing the patient. Thus, urine meter 10 may be removed with minimal discomfort to the patient.

Referring to the structure of container 12, the front wall 22 may have a vent 82 formed therein adjacent inlet 32 to allow the flow of urine into and through urine meter 10. As is apparent, the vent may be located elsewhere such as in the front wall 22 adjacent the outlet 64 or in rear wall 24. The vent is designed to allow air to flow into and out of container 12 but prevents liquids, such as urine, from escaping the container through the vent.

Figure 3:
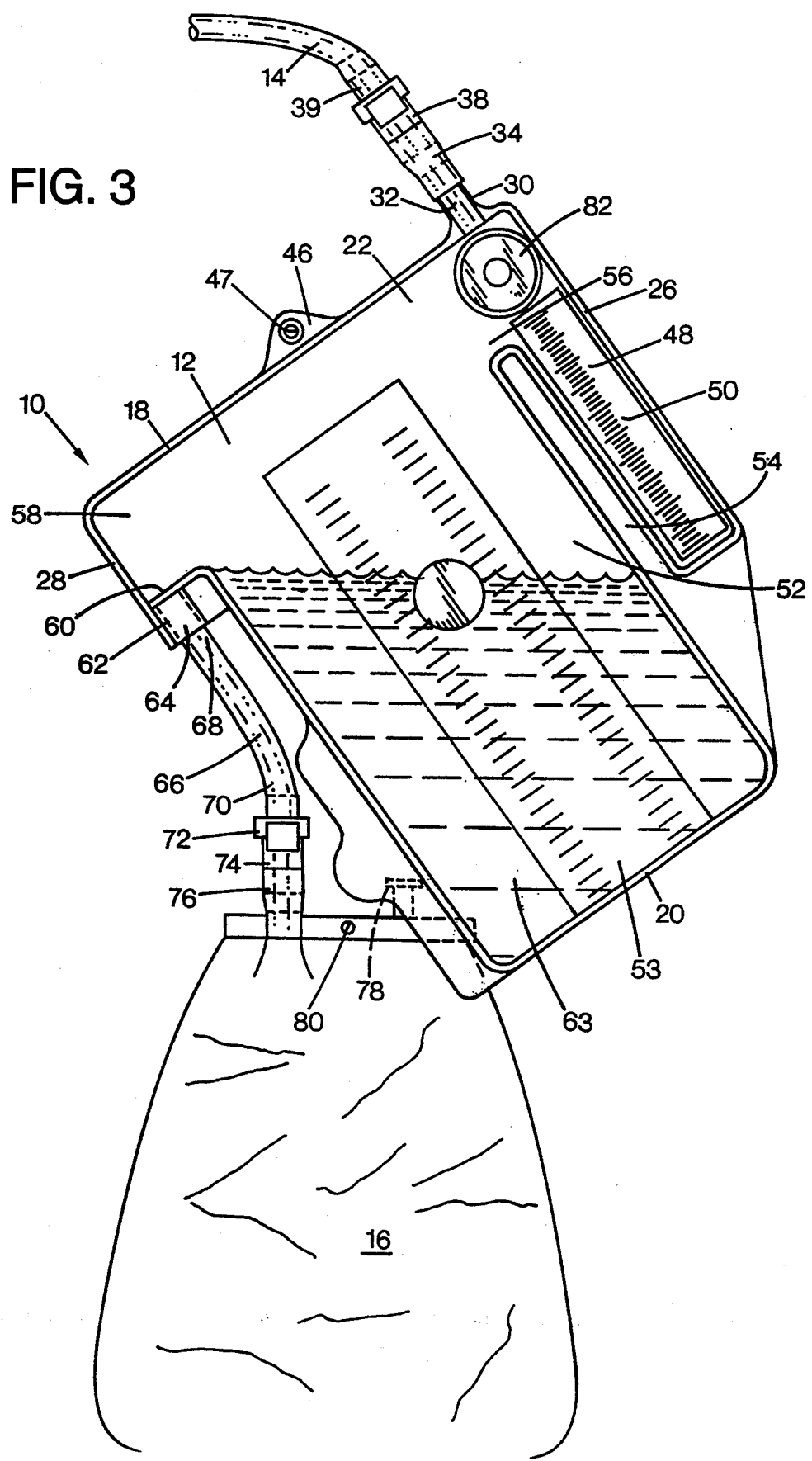
FIG. 3 is a front view of the fluid meter of FIG. 1 in a tilted position for emptying fluid into the collection bag.

The fluid meter 10 of the present invention thus provides a novel method for collecting and measuring fluid such as urine from a patient. If the particular purpose is to measure urine flow, the drain tube 14 is connected to the inlet of the meter and the collection bag is connected to the outlet of the meter. Urine is then measured as it fills container 12. If the container 12 is filled close to capacity, it is tilted as shown in FIG. 3 to discharge the urine into bag 16. If it is desirable to remove the meter 10 because, for example, urine measurement is no longer required for a patient, the meter is simple disconnected from the tube 14 and the bag 16. The tube and bag may then be connected together because of the nature of their connectors as explained above. On the other hand, it may be desirable to change the bag 16 occasionally as it becomes used without removing the meter 10. This procedure is also simple to perform by disconnecting a present bag from the meter 10 and connecting another bag.

While the present invention has been described with reference to a preferred embodiment, it is to be understood that it is the claims that define the scope of the invention. Substitutions and alterations may be made to this embodiment without departing from the spirit and scope of the invention as set forth in the following claims.

I claim:

1. A fluid meter for insertion between a catheter drain tube and a fluid collection bag, comprising:
    a container having an inlet and an outlet, the container including a first chamber adjacent to the inlet for receiving fluid therefrom and a second chamber adjacent to the outlet, the first chamber in fluid communication with the second chamber; and
    a first connector operatively attached to the container outlet for connecting the container to and disconnecting the container from a fluid collection bag, the first connector being one part of a two part connector, the other connector part being attached to the fluid collection bag;
    the second connector being one part of a two part connector, the other connector part being attached to the drain tube; and
    the first and second connectors being constructed such that the connector part attached to the drain tube is adapted to connect to the connector part attached to the fluid collection bag with the fluid meter disconnected from the drain tube and fluid collection bag.

2. The fluid meter of claim 1 wherein the first connector is a male connector part and the second connector is a female connector part for connecting to such a male connector part.

3. The fluid meter according to claim 1 including a tube disposed between the container outlet and the first connector for discharging the fluid in the container into the fluid collection bag.

4. The fluid meter of claim 1 wherein the container has a top, bottom, front, rear and opposite side walls, the top wall having the inlet formed therein and one of the side walls having the outlet formed therein.

5. The fluid meter of claim 4 wherein the container has a vent extending through the front wall to permit ingress of air into the container.

6. The fluid meter of claim 4 wherein the outlet extends outwardly towards the bottom wall of the container.

7. The fluid meter of claim 1 wherein the inlet and outlet each has a longitudinal axis, the longitudinal axis of the inlet being substantially parallel to the longitudinal axis of the outlet.

8. The fluid meter of claim 1 wherein the fluid is urine.

9. A urine meter for insertion between a catheter drain tube and a urine collection bag to measure fluid, comprising:
    a container having an inlet and an outlet, the container including a first chamber adjacent to the inlet for receiving and measuring urine therefrom;
    a first connector operatively attached to the container outlet for connecting the container to and disconnecting the container from a urine collection bag, the first connector comprising one part of a two part connector, the other connector part being attached to the urine collection bag;
    a second connector operatively attached to the container inlet for connecting the container to and disconnecting the container from a catheter drain tube, the second connector comprising one part of a two part connector, the other connector part being attached to the drain tube; and
    the first and second connectors being constructed such that the connector part attached to the drain tube is adapted to connect to the connector part attached to the urine collection bag with the urine meter disconnected from the drain tube and urine collection bag.

10. The urine meter of claim 9 wherein the container includes the first chamber adjacent to the inlet for receiving urine therefrom and a second chamber adjacent to the outlet, the first chamber in fluid communication with the second chamber.

11. The urine meter of claim 9 wherein the container has a top, bottom, front, rear and opposite side walls, the top wall having the inlet formed therein and one of the side walls having the outlet formed therein.

12. A method of collecting and measuring fluid from a patient who has a catheter and a drain tube attached to the catheter comprising the steps of:

if measuring fluid flow, connecting the drain tube to a fluid meter and the fluid meter to a fluid collection bag;

if changing the fluid collection bag, disconnecting the fluid meter from the fluid collection bag and reconnecting another fluid collection bag to the fluid meter; and if removing the fluid meter, disconnecting the drain tube and fluid collection bag from the fluid meter and connecting the drain tube to the fluid collection bag.

13. The method of claim 12 wherein the fluid is urine.

14. A fluid meter for insertion between a fluid source and a fluid collector to measure fluid, comprising:

a container having an inlet and an outlet, the container including a first chamber adjacent to the inlet for receiving and measuring fluid therefrom;

a first connector operatively attached to the container outlet for connecting the container to and disconnecting the container from the fluid collector, the first connector comprising one part of a two part connector, the other connector part being attached to the fluid collector;

a second connector operatively attached to the container inlet for connecting the container to and disconnecting the container from the fluid source, the second connector comprising one part of a two part connector, the other connector part being attached to the fluid source; and the first and second connectors being constructed such that the connector part attached to the fluid source is adapted to connect to the connector part attached to the fluid collector with the fluid meter disconnected from the fluid source and fluid collector.

* * * * *

UNITED STATES PATENT AND TRADEMARK OFFICE
CERTIFICATE OF CORRECTION

PATENT NO. : 5,409,014
DATED : April 25, 1995
INVENTOR(S) : Napoli et al

It is certified that error appears in the above-indentified patent and that said Letters Patent is hereby corrected as shown below:

Column 1, line 60, after "collecting" insert --urine--. The fluid meter includes a container having an --.

Signed and Sealed this

Twenty-fourth Day of October, 1995

BRUCE LEHMAN

Attest:

Attesting Officer          Commissioner of Patents and Trademarks